United States Patent
Alliger

[19]
[11] Patent Number: 6,039,934
[45] Date of Patent: Mar. 21, 2000

[54] USE OF XANTHAN GUM FOR GELLING $ClO_2$ AND RELATED SPECIES

[76] Inventor: Howard Alliger, 10 Ponderosa Ave., Melville, N.Y. 11747

[21] Appl. No.: 09/128,898

[22] Filed: Aug. 4, 1998

[51] Int. Cl.[7] .............................. A61K 7/20; A61K 33/20
[52] U.S. Cl. .............................................. 424/53; 424/661
[58] Field of Search ................................ 424/49–58, 661

[56] References Cited

U.S. PATENT DOCUMENTS

| | | |
|---|---|---|
| 4,861,514 | 8/1989 | Hutchings . |
| 4,891,216 | 1/1990 | Kross et al. . |
| 5,051,252 | 9/1991 | Schultz et al. ............................. 424/71 |

FOREIGN PATENT DOCUMENTS

| | | |
|---|---|---|
| 2290233A | 12/1995 | United Kingdom . |
| 98/04235 | 2/1998 | WIPO . |

OTHER PUBLICATIONS

The NutraSweet/Kelco Company; Xanthan Gum; Natural Biogum for Scientific Water Control; 1994; pp. 1–24.

Dobosz, L.M. and Holmes, T.J. Handling of Sodium Chlorite with Plastics; Development of a Liner for a Rail Car Tanker; Oct. 1997; pp. 34–40.

Allen, Lloyd V. Commercial Literature; www.paddocklabs.com; 1994; pp. 1–12.

*Primary Examiner*—Shep K. Rose
*Attorney, Agent, or Firm*—Henry D. Coleman; R. Neil Sudol

[57] ABSTRACT

The invention described relates to gelled chlorine dioxide compositions comprising water, an acid, a water-soluble chlorite salt and a gelling agent in two parts A and B, wherein the gelling agent is xanthan gum or a mixture of xanthan gum and an acid stable gelling agents. Compositions according to the invention are storage stable for at least 6 months, preferably at least about year.

20 Claims, No Drawings

USE OF XANTHAN GUM FOR GELLING ClO$_2$ AND RELATED SPECIES

FIELD OF THE INVENTION

The present invention relates to the utilization of a gelling material whose special properties lend itself to the disinfection of skin and wounds using chlorine dioxide (ClO$_2$) and related species as disinfectant agents while overcoming the difficulties (related to instability) of extreme pH and high salt (especially chlorite) concentration. Furthermore the gel is resistant to oxidative attack by the active ingredients, namely chlorine dioxide and related species.

DESCRIPTION OF PRIOR ART

In 1978, the present inventor's U.S. Pat. No. 4,084,747, showed that chlorine dioxide and chlorous acid could be released, when, and as needed, by mixing small quantities of sodium chlorite, (Part A), with a weak acid, (Part B). Both parts were in liquid form. The purpose of this in situ process was for applications such as disinfecting the skin, curing disease, reducing inflammation, and germicide treatment of surfaces and medical hardware. Since the resulting active ingredients are unstable and highly reactive, the 2 parts are not combined until needed. The '747 patent of the present inventor appears to have since spawned about 200 or more other ClO$_2$ patents in similar applications.

In earlier attempts at improvement by the present inventor, the methology of the '747 patent was improved by incorporating the reacting components of the formula in 2 gels rather than 2 liquid parts. This improvement was patented as U.S. Pat. No. 4,330,531. The gel form is more convenient and easier to mix for topical application, and also shows improved efficacy in killing bacteria on the skin.

The 2 foregoing patents lived up to their promise in that all microorganisms were killed in a few minutes—probably faster than by any other way, and when applied to the skin, ear or mouth, the ClO$_2$ compounds did not cause irritation or adverse effect. Also importantly, due to the moderate acidity and slow release of active ingredients, the disinfectant remained active for many hours.

Although fast disinfection and non-toxicity are not normally found side-by-side in the same compound, this combination of effects was achieved by the methods of these 2 patents, and many small in vitro ClO$_2$ processes now exist for disinfecting environmental surfaces. However, with all the research in the ClO$_2$ field the past 20 years, no ClO$_2$ gel system became practical for disinfecting the skin, and in particular, curing disease. In the case of my own '531 gel patent, the best gelling agent given was methyl cellulose, technically a polysaccharide derivative. This material showed great promise at first, solubilizing both the acid Part at pH 1.9, and chlorite Part at pH 12.5, in clear, thick, easily mixed gels. Unfortunately, in less than 6 months both the pH and viscosity of the gelled material changed radically, especially in the alkaline, chlorite part, wherein the viscosity was significantly reduced to be almost useless. If stored or shipped above room temperature, the unwanted changes in the methyl cellulose gel occurred even faster. Changes in the acid Part B were slower, but could be noticed in 6 months.

One possible exception to the lack of practical gel ClO$_2$ applications was the incorporation of a dual, ClO$_2$ releasing system for the prevention of mastitis, sold commercially as a teat dip for cows as disclosed by Kross, in U.S. Pat. No. 4,891,216. The "gel" utilized in this narrow application however, is quite waterlike and flows easily. There is little or no build up of jelly-like material when the compound is placed on the skin or teat. The chlorite part at high pH in this patent is solubilized by polysulfonic acid (trade name, Rheothik), a thick fluid, like honey, rather than a standard gelling material.

Gelling agents such as methyl cellulose, carbopol, acrylamide or tragacanth, on the other hand, begin as a powder. When the powder is mixed with water, dissolved polymers become interlaced or crosslinked and a semisolid results. In the same polysulfonic patent '216, the second part, at low pH, is gelled by hydroxyethyl cellulose (Natrosol) which is capable of gelling in the normal way but must be made thin in this case so as to match the low viscosity of part A. The acid viscosity of the Part B mixture starts at about 800 cps and becomes lower in time. A non-viscous final product for a teat dip may apparently be desirable, but could not be made more gel-like, if necessary, without an undue high percentage of the polysulfonic liquid.

For example, another polysulfonic acid (see U.S. Pat. No. 4,891,216), for the treatment of acne, requires a high 45% Rheothik. The liquid raw material would be expensive compared to one of the more common gelling agents, but also relatively difficult to handle and formulate since the initial viscosity is about 400,000 cps. A cellulose type gelling material, starting as a powder, normally makes a thick gel at only 2% concentration. There are other difficulties with Rheothik in ClO$_2$ applications. First, the liquid is an acid and needs to be neutralized, and then brought to the appropriate pH of 12.5 in order to accommodate the ClO$_2^-$. Second, as pointed out, Rheothik cannot be used to incorporate the acid, part B, so again Natrosol is used for this purpose. Because of the difference in consistency and rheological properties of the disparate 2 materials, it is not easy to dispense and mix the two dissimilar gels evenly, except at low viscosities. For topical use, thick gels are usually mixed in the palm of the hand or in the edge of a sink. Finally, the acid Part B gel using hydroxyethyl cellulose will lose about ¾ of its viscosity in 9 months due to the chemical attack of low pH.

However, despite these clear drawbacks, Rheothik appeared to be the only reagent which could stabilize a gel containing sodium chlorite, apparently due to the high pH and oxidizing potential of the mixture. The inherent stability of Rheothik seemed appropriate since polysulfonic acid is not oxidizable by ClO$_2^-$, or ClO$_2$, as are most gels, especially organic gels. Also, Rheothik at high pH does not catalyze the release of ClO$_2$ from the dissolved ClO$_2^-$, as do most other gels, organic or inorganic.

Chlorite is unstable in most situations and conditions, and is strongly effected by light, and heat, as well as pH, organics and trace metal ions. Handling of liquid sodium chlorite in tank cars, for example, was the subject of much research. The usual plastic liners in railroad cars are inadequate to ship chlorite. Protective liner materials such as polyethylene, polyurethane, most vinyls and epoxies, chloroethylene, 304 stainless steel, and all rubbers, are attacked by the chlorite. In this research, a particular composite of Fiberglass Reinforced Plastic was finally chosen which was described as, "sufficiently resistant" for use as the rail car lining (from: *Handling of Sodium Chlorite with Plastics: Development of a Liner for a Rail Car Tanker,* L. M. Dobosy, T. J. Holmes).

U.S. Pat. No. 4,861,514 to Hutchings discloses a chlorine dioxide-containing composition at high pH (i.e. greater than 7.0 and preferably above about 11.0), comprising sodium chlorite and an initiator. Interestingly, Hutchings contends that he utilizes a number of thickeners, including xanthan gum in the composition at high pH to initiate the formation of chlorine dioxide. In Hutchings, the initiator is used to react with and otherwise interact with the chlorite to produce chlorine dioxide. Hutchings does not disclose a storage stable system based upon the inclusion of xanthan gum in combination with chlorite because such a system is incompatible with the teachings of Hutchings. In addition, Hutchings fails to mention the desirability of utilizing xanthan gum in a storage stable two part A and B system, which provides for storage stability for both the chlorite (A) part and the acid (B) part. In addition, Hutchings fails to even mention the desirability of combining a two part system under acidic conditions to generate chlorine dioxide. Further, xanthan gum is not an initiator, and the present inventor utilizes xanthan gum for the opposite property of no chemical interaction.

Objects of the Invention

It is an object of the present invention to provide a two-part viscous storage stable chlorine dioxide generating system which is storage stable for at least about 6 months.

It is another object of the invention to provide a storage stable chlorine dioxide generating composition which can generate high concentrations of chlorine dioxide at a pH of less than about 5.5.

These and other objects of the present invention may be readily gleaned from the description of the present invention which follows.

BRIEF DESCRIPTION OF THE INVENTION

The present invention relates to a storage stable chlorine dioxide generating composition comprising a chlorite-containing part (A) and an acid-containing part (B), said chlorite-containing part (B) comprising about 0.1% to about 5%, more preferably about 0.5% to about 2% weight of a water-soluble chlorite salt in solution and an amount of xanthan gum effective to gel said solution, said acid-containing part (B) comprising an amount of a protic acid in solution effective to produce an initial pH upon combining and mixing said parts A and B of less than about 5.5 and an amount of a gelling agent effective to gel said part B, said parts A and B being storage stable for a period of at least about 6 months.

The overall pH range of compositions according to the present invention ranges from less than about 1.8 to about 5.5, more preferably about 2.0 to about 4.5. In the case of topical gel formulations, the pH ranges from slightly less than about 2.8 to about 5.0 (i.e., compatible with topical delivery to an animal or human or no less than about pH 2.5), preferably about 3.0 to about 4.5. In the case of chlorine dioxide solutions for use in disinfecting medical and dental instruments, the initial pH (after initially combining the A and B parts) ranges from about 3.5 to about 4.5–5.0.

Preferred compositions according to the present invention generate a desired concentration of chlorine dioxide, of preferably at least about 5 parts per million (ppm) and preferably at least about 25 ppm of chlorine dioxide from chlorous acid within a period of no greater than about 15 minutes after mixing. Of course, the amount of chlorine dioxide which is produced within the initial 15 minute period may be substantially greater than 5 ppm. By definition, 1 part per million is equal to 0.0001% by weight. Compositions which can produce concentrations of chlorine dioxide of 100 ppm or more are also contemplated by the present invention and are preferred. The rate of chlorine dioxide production and the concentration of chlorine dioxide which is produced upon mixing of the A and B parts may be affected by the strength (pKa) and concentration of the acid used, the concentration of chlorite salt within part A, the absence or inclusion of a disproportionation agent or other agent which increases the rate of formation of chlorine dioxide, among other factors.

Compositions according to the present invention may be used in various applications, including, for example, as topical biological disinfectants and pharmaceutical agents, primarily for use on the skin and to disinfect surfaces where it would be desired to disinfect such surfaces, such as surgical and medical equipment, equipment which comes into contact with food, among numerous other applications.

The special properties which preferably should be exhibited by a gel for a topical application, to be used as a disinfectant or pharmaceutical formulation, are unusual and many. The following lists the preferred characteristics of compositions according to the present invention which are to be used in topical skin applications (in animals, including humans), some briefly stated before:

Establishing a 2 gel system, one to be stable at a pH of about 12.5, and the second at a pH of preferably of about 1.9, and on a long term basis. The mixed gels have an initial pH preferably of about 2.8–5.5, more preferably about 3–4, where both gels must be stable.

The gelling capacity in Part A should not be greatly effected by high salt or electrolyte concentration of the chlorite and its carbonate and hydroxide stabilizers. Each gel should have a viscosity of at least about 500–1,000 cps, preferably at least about 2000 cps, more preferably about 2,000–15,000 and even more preferably about 20,000 to about 25,000 up to about 35,000 cps or more.

Each gel should be easily dispensed and easily mixed together in the palm of the hand. When applied topically to the skin, wound, or infection, the combined gel should not drip or run.

For best consumer appeal, the gels should preferably be clear and non greasy. Transparency gives the look of purity. The clear gels also appear to sink into the skin faster.

The gel must be non-irritating, compatible with the skin and should not inhibit wound healing. It must leave little or no residue. The gel should not interfere with the disinfecting ability of the released $ClO_2$ and related oxidants (as do many wetting agents).

The gel in Part A, pH 12.5, incorporating chlorite, $ClO_2^-$, must be resistant to oxidation on a long term basis. Also the gel must not catalyze the release of chlorine dioxide from the dissolved chlorite (as many metal ions and wetting agents will do).

The combined gel should not be attacked by the released $ClO_2$ which is a strong oxidant.

Separately, both gels A & B should be stable for at least six months and preferably for over a year at room temperature and evidence little loss in viscosity, little change in pH, and little or no release of $ClO_2$ in the chlorite gel.

Methods of making a storage stable chlorine dioxide-containing composition utilizing xanthan gum and increasing the stability of a gelled chlorine dioxide generating composition comprising added an effective amount of xanthan gum to said composition are also contemplated by the present invention.

DETAILED DESCRIPTION OF THE INVENTION

The term "storage stable" is used throughout the specification to describe two part gelled chlorine dioxide generating compositions according to the present invention which may be stored for periods of at least six months, preferably at least one year and in certain cases as long as 18 months or longer at room temperature without appreciably affecting the ability of the composition when both parts are combined to generate of chlorine dioxide or lowering the viscosity of the compositions.

The term chlorite" or "chlorite salt" is used throughout the specification to describe a salt of chlorite which is readily soluble in an aqueous system and which readily dissociates into chlorite anion and counterion (generally, metal). Two particularly preferred salts of chlorites for use in the present invention include sodium chlorite and potassium chlorite.

The term "acid" is used throughout the specification to describe protic acids, i.e., acids that release hydrogen ions in solution. Acids for use in the present invention include strong inorganic acids such as hydrochloric, sulfuric and nitric acid, benzenesulfonic acid, among other organic sulfonic acids, which, depending upon the end-use of the composition, may be preferably included as dilute acid, organic acids such as citric, fumaric, glycolic, lactic, malic, maleic, tartaric acid, citric, propionic, acetic and mandelic, among others, including ethylenediaminetetraacetic acid (EDTA, as the free acid or the monosodium salt), among others and inorganic acids such as sodium and potassium bisulfate (NaHS04 and KHS04) and phosphoric acid, among numerous others. It is noted that numerous additional acids may also be used in the present invention. In its broadest aspect, compositions according to the present invention may make use of virtually any acid, to the extent that it provides an initial pH, which when the chlorite-containing A part and the acid-containing B part are combined produce an initial pH of less than about 5.5. One of ordinary skill will be able to readily determine the type and amount of acid to be used for a particular application.

The term "chlorite part" is used throughout the specification to describe the form in which an amount of a water soluble salt of chlorite either in dry or liquid state (preferably, as an aqueous solution) is added to the acid part. In general, the chlorite part (A) is added to the acid part (B) and preferably, both the chlorite part A and the acid part B are mixed together in an aqueous solution to which has been added effective amounts of gelling agents.

The term "acid part" is used throughout the specification to describe the form in which an amount of a water soluble low pKa acid either in dry or liquid state is added to the chlorite part. Preferably, the acid part (B) is premixed and is in the form of an aqueous solution which is combined with chlorite part (A) which is also preferably in the form of an aqueous solution to produce chlorine-dioxide generating compositions.

The term "gelling agent" is used throughout the specification to describe a compound or composition which is added to the present compositions in order to increase the viscosity of the composition. Gelling agents which are used in the present invention may be added to the chlorite-containing part (A) or the acid-containing part (B) in amounts effective to gel the solution to which these compounds have been added. It is noted that when adding a gelling agent to the chlorite-containing (A) part, xanthan gum is the only common carbohydrate (biocompatible) gelling agent found by the inventor to be able to withstand the high pH and oxidative strength of the solution to produce a gelled composition having a viscosity within the desired range of the present invention, i.e., of at least about 100–200 cps, preferably at least about 500 cps, more preferably at least about 1000 cps, still more preferably about 2,000–15,000, and even more preferably about 20,000–25,000 up to 60,000 cps or more, depending upon the end use for which the composition is to be used. For example, in the case of toothpastes, the composition will have a higher viscosity, preferably about 15,000–60,000 cps or more. In the case of more liquid soaps or shampoos, the viscosity preferably will be between about 5,000 and 10,000 cps. In the case of teat dips, the viscosity may fall within the range of about 100 cps to about 1,000 cps or more. One of ordinary skill readily will be able to modify the compositions according to the present invention in order to adjust the viscosity to provide numerous end uses. In the case of gelling agents which may be added to part (B), these are acid stable gelling agents.

Gelling agents for use in the acid part (B) of the present invention include the preferred gelling agent, xanthan gum, as well as other relatively acid stable gelling agents such as natural and synthetic gelling agents including polysaccharides extracted from legume seeds, such as the galactomannans, including guar gum and locust bean (carob) gum. Other gelling agents include high molecular weight polyoxyalkylene crosslinked acrylic polymers as well as the highly preferred cellulosics such as hydroxymethyl cellulose, hydroxypropyl cellulose, hydroxyethyl cellulose, methyl cellulose, methylpropyl cellulose, among others, including high molecular weight polyethylene glycols, polyacrylamide gels and crosslinked polyvinylpyrrolidones, among others. It is preferred that the gelling agent in the acid-containing part B should be stable to pHs ranging from less than about 2 (even as low as 1.0, depending upon the acid used) to about 5.5 so that the gelling agent can be used in all formulations (including Parts A and B and the mixture of both).

The term "xanthan" gum is used throughout the specification to describe the gelling agent used in the chlorite-containing part A and is a preferred gelling agent used in the acid-containing part B of the two part compositions according to the present invention. Xanthan gum is a complex carbohydrate produced by the bacterium, *Xanthomonas campestris*. It is comprised of xanthan gum repeat units. Each xanthan gum repeat unit contains five sugar residues: two glucose, two mannose and one glucuronic acid. The polymer backbone of xanthan gum is made up of 1,4-linked β-D-glucose, which is identical to the structure of cellulose. Xanthan has, in addition to a cellulose-like backbone, trisaccharide side chains on alternating anhydroglucose units. Each side chain contains a glucuronic acid residue between two mannose units. At most of the terminal mannose units is a pyruvate moiety. The mannose group nearest the main chain carries a single acetyl group at C-6.

The molecular weight of xanthan gum may range from about 1,000,000 (preferably, at least about 2,000,000) dalton units to above about 50,000,000 dalton units per polymer molecule. The differences may be due to polymer chain association. It is noted that certain processed xanthan gum may obtain molecular weights outside of the above-described weight ranges. Xanthan gum is available from a number of commercial sources including the Kelco Division of Merck & Co., Inc., San Diego, Calif., Chicago, Ill. and Clark, N.J., USA and Shin-Etsu Biochem, Inc., San Diego, Calif., among other suppliers and available under the tradenames KELTROL (as well as KELTROL T, TF, F, BT, GM, RD and SF), KELZAN, KELFLO and others. Preferably, KELTROL is the xanthan gum product used in compositions according to the present invention.

The term "gel composition" or "gel" is used to describe an aqueous composition according to the instant invention which includes an amount of a gelling agent effective for gelling the composition, i.e., to obtain a viscosity of at least about 500 cps, preferably at least about 1000 cps, more preferably about 2,000–15,000, and even more preferably about 20,000 up to about 25,000 cps or more. Gel compositions are preferred for topically delivering chlorine dioxide to a site in need of disinfection or chlorine dioxide therapy. In general, the amount of a gelling agent included in the aqueous chlorine dioxide generating compositions according to the present invention ranges from about 0.05% to about 5–6% (or more) by weight of the composition, with a preferred amount of gelling agent falling within the range of about 0.5% to about 4%, even more preferably about 1% to about 4% by weight.

The term "effective amount" is used throughout the specification to describe a minimum amount, quantity or concentration of a component, i.e., an acid, chlorite salt, gelling agent, or other component or additive such as a disproportionation agent which is included in a composition to produce or generate an intended effect, e.g., a concentration of chlorine dioxide or to gel the composition for its use as a topical composition. The term effective amount when used to describe the acid, is used to describe that amount of acid, either in dry or liquid form which, when combined with chlorite in solution, will produce an initial pH of below about 5.5, preferably about 1.8 to about 4.5, even more preferably about 2.6 to about 4.5, and even more preferably about 3 to about 4.2. Soap and toothpaste formulations will be at the higher pHs of these ranges.

The present invention relates to a storage stable chlorine dioxide generating composition comprising a chlorite-containing part (A) and an acid-containing part (B), said chlorite-containing part (B) comprising about 0.1% to about 5%, more preferably about 0.5% to about 3.0%, even more preferably about 1% to about 2% by weight of a water-soluble chlorite salt in solution and an amount of xanthan gum effective to gel said solution, said acid-containing part (B) comprising an amount of a protic acid in solution effective to produce an initial pH upon combining and mixing said parts A and B of less than about 5.5 and an amount of a gelling agent effective to gel said part B, said parts A and B being storage stable for a period of at least about 6 months, more preferably for at least a year or more (in certain cases, the compositions according to the present invention may be storage stable for periods of at least 18 months to 24 months or even longer). A two-part composition is contemplated as is the combined composition which contains a mixture of A and B, preferably an equal mixture of A and B for ease of production and administration.

The initial pH of compositions which comprise mixtures of a chlorite-containing part A and an acid-containing part B according to the present invention ranges from less than about 1.8 to about 5.5, more preferably about 2.0 to about 4.5. In the case of topical gel formulations, the pH ranges from slightly less than about 2.8 to about 5.0 (i.e., compatible with topical delivery to an animal or human or no less than about pH 2.5), preferably about 3.0 to about 4.5. In the case of chlorine dioxide solutions for use in disinfecting medical and dental instruments, the initial pH (after initially combining the A and B parts) ranges from about 3.5 to about 4.5–5.0. It is noted that the initial pH will tend to increase over time, but will generally stay within the range of an acidic pH and generally, less than about 5.5.

Preferred compositions according to the present invention generate a desired concentration of chlorine dioxide, of at least about 1 part per million (ppm) and preferably at least about 5 ppm of chlorine dioxide from chlorous acid within a period of no greater than about 15 minutes after mixing. Of course, the amount of chlorine dioxide which is produced within the initial 15 minute period may be substantially greater than I ppm or 5 ppm, even as high as several hundred parts per million or more. The rate of chlorine dioxide production and the concentration of chlorine dioxide which is produced upon mixing of the A and B parts may be dramatically affected by the strength (pKa) and concentration of the acid used, the concentration of chlorite salt within part A, the absence or inclusion of a disproportionation agent or other agent which increases the rate of formation of chlorine dioxide, among other factors. Where the pKa of the acid is lower, the stronger acid will tend to release chlorous acid and chlorine dioxide more quickly than do acids which have a higher pKa. Likewise, higher concentrations of chlorite will tend to release chlorous acid and chlorine dioxide more quickly than do lower concentrations of chlorite. The reaction of chlorite with an acid to produce chlorine dioxide is explained by the equations which are set forth below.

When an acid is combined with sodium chlorite, chlorous acid is formed:

1) $H^+ + NaClO_2 \rightarrow HClO_2 + Na^+$

Chlorous acid is unstable and disproportionates yielding chlorine dioxide:

2) $5HClO_2 \rightarrow 4ClO_2 + HCl + 2H_2O$

With a sufficient amount of sodium chlorite and at a pH not too low, a steady supply of chlorous acid will be produced in equation 1, as it is used up in equation 2. This prolonged release assures that the disinfection ability will be maintained over a period of many hours. In our gel system, a pH between 3 and 4 is ideal for topical application. On the other hand, if a strong acid is used at a low pH, a great deal of chlorine dioxide will evolve immediately and the disinfection system will be short lived. If the pH is too high, for example above about pH 5.5, very little chlorous acid will be produced, and in turn, little chlorine dioxide, as set forth in equation 2.

Since gel compositions according to the present invention in the 3–4 pH range kill all bacteria within one minute, much faster than just $ClO_2$ alone, it is possible that a chlorous acid/chlorine dioxide complex is formed. This may be the reactive complex producing the extraordinary speed of microorganism deactivation. At too high or too low a pH the ideal ratio of chlorous acid to chlorine dioxide may be lost, with a concomitant reduction in disinfectant activity. A large amount of $ClO_2$ in the gel does not kill bacteria faster, and in fact may be detrimental in this regard. Too much $ClO_2$ may also be irritating when applied to a wound.

It is an unexpected result that xanthan gum can be used as an effective gelling agent alone to produce a storage stable part A for use in the present invention. This is particularly surprising given the high pH to which the xanthan gum is subjected to in the chlorite part A of the present compositions. The pH of part A preferably ranges from about 11.0 to about 13.0 or higher, even more preferably about 12.5. A high pH is maintained in Part A because high pH stabilizes the chlorite. For this reason, chlorite solution is shipped by the original producer at about this pH. It is somewhat unclear as to why so high a pH is necessary, but the alkalinity possibly prevents any "stray" $H^+$ ions from combining with chlorite to form chlorous acid then chlorine dioxide. If $ClO_2$ is formed, then HCl is also formed, as in equation 2, which lowers the pH and causes the chlorite to be even less stable.

Chlorine dioxide attacks almost all gel systems and causes the viscosity to be significantly reduced over time. It attacks the cellulose "backbone" in gels such as hydroxy ethyl cellulose, causing both a lowering of viscosity and pH. Chlorite, even when stabilized at high pH, will at least slowly oxidize almost all organics. As a result of oxidation, carboxylic acid is possibly released which will combine with $ClO_2^-$ to form chlorous acid, and so hasten the degradation process. At a pH of less than 10.5 this regenerative feedback proceeds quickly, often to well below pH 7 in a matter of weeks.

Some gelling materials are fairly resistant to $ClO_2$ and $ClO_2^-$, but none of these, however, will gel at high or low pH, or high salt content. For instance Carbopol and acrylamide, both non-cellulose gels, are resistant to oxidation but will not gel at pH 2 and 12.5. Inorganic Veegum, a magnesium aluminum silicate gel, and silicon dioxide gels, release chlorine dioxide when in contact with the chlorite. Alginate and agar are particularly prone to oxidation, sometimes giving off acid fumes. PVA gels are oxidized as well, by chlorite. When gelling $ClO_2^{3^1}$, tragacanth gum is not stable above pH 9.

It was a surprise to find a common and inexpensive gelling agent, xanthan gum, that fullfills all the chemical and physical requirements cited previously. This discovery is all the more surprising since the xanthan gum molecule has a repeat unit that consists of a cellulose backbone with a trisaccharide side chain, the presence of the cellulose backbone being associated with instability in other gelling agents. Previous experience would indicate that strong oxidizing agents like persulfates, peroxides, and hypochlorites depolymerize xanthan gum. However, the present inventor has found xanthan gum to be suprisingly stable when gelled with chlorite. Evaluations of the gel after 10 months showed that pH and viscosity were reduced only slightly. In the acid part B, there was no change detectable at all. In addition, no $ClO_2$ was released from the chlorite, part A.

While not being limited by way of theory, it is believed that the unique structure of xanthan gum provides protection from oxidation and high pH of the chlorite-containing part A. Most industrial gums are derived from botanical sources. Xanthan gum however, is a microbial polysaccharide, produced in a fermentation process from the bacterium, Xanthomonas campestris. Although xanthan's polymer contains a cellulose group similar to methyl cellulose or hydroxymethyl cellulose, apparently the cellulose backbone is protected by its unique side chains when exposed to acids, alkalis, and to chlorite. This gives xanthan gum its superior stability compared to other polysaccharides.

The amount of xanthan gum used in the chlorite-containing part A typically ranges from about 0.05% to about 5%, more preferably about 0.2% to about 3% by weight, and for most skin and wound application it is about 2%, resulting in about a viscosity of about 20,000 cps. In the acid part B, xanthan gum is preferably used as the gelling agent and the same weight range of xanthan gum may be used in the part B composition as in the part A composition. For a less viscous composition, particularly suitable as a liquid soap, shampoo, or as a teat-dip for treating cows, the amount of xanthan gelling agent may be from about 0.2% to 1.3%. A toothpaste is more viscous with a concentration of about 2.5% xanthan.

The concentration of sodium chlorite in the final composition is about 0.1% to about 5% or more, but preferably ranges from about 0.5% to about 2%, more preferably about 0.5% to about 1% within this range. The pH of the gel containing chlorite (part A) is generally greater than 11 and preferably from about 11.5 to 12.5 or even higher. The pH of the acid, in part B, for example will range from about 1.5 to about 5.5%, with a preferred range of about 2.0 to about 4.5, even more preferably within the range of about 2.2 to about 3.5. Any number of acids may be used in the present invention and the particular acid chosen and the concentration of such acid will determine the pH of a solution into which such acid will be added. For example, the pH of a phosphoric acid solution will usually fall between about 1.8 and 3.0. After the gels are mixed, the pH of the resulting composition may preferably be between about 2.8 and 4 for skin and wound disinfection.

Besides application as a skin and wound disinfectant, the xanthan dual gel system, as mentioned, can be formulated into a toothpaste, into a soap, and also into a disinfectant shampoo. In addition, disinfectant gels which are used on surfaces to be disinfected are also contemplated by the present invention. The separate gels of parts A and B can conveniently be dispensed from an epoxy type syringe which may be fitted with a small mixing tube at the end. It is also possible to dispense the gels from a tube or bottle with 2 containers within, and then 2 streams are released with one stroke or squeeze.

In addition to chlorite, acid and gelling, compositions according to the present invention may include at least one or more additive selected from the group consisting of disproportionation agents (including, for example, aldehyde disproportionation agents) as well as a number of additives which are commonly used in cosmetic and pharmaceutical formulations including surfactants, emollients, wound healing agents, lubricants, film-formers, diluents, fillers, humectants, fragrances, flavorings and skin penetrants. These additives include, for example, surfactants such as sodium lauryl sulfate, Nacconol™, and poloxamer™ (polyoxypropylene/polyoxyethylene block copolymer), among numerous otherss, such as lanolin and glycerol monostearate, among others, glycerine, propylene glycol and ethyl alcohol. These additives are generally included in effective amounts ranging from about 0.025% to about 8% by weight or more of the part to which the additive is included. These components are selected for their stability. Glycerine is a particularly useful additive. It is natural to the body and a good emollient. It also functions to protect the skin when it is subject to high concentrations of $ClO_2$. Compositions according to the present invention utilize glycerine in effective amounts (ranging from 0.5% to about 20–25% or more, more preferably about 20% by weight). Fragrances may also be advantageously employed in amounts ranging from about 0.01% to about 1% by weight or more, although a number of fragrances tend to be oxidizable. Skin penetrants may also be employed to quickly dissolve the active ingredients and enhance the effect of topically administered chlorine dioxide by enhancing their skin penetration.

A toothpaste formula according to the present invention can incorporate titanium dioxide fine powder or other polish powders for better tooth cleaning. The soap and shampoo should best have wetting agents or detergents that foam and lather especially well because $ClO_2$ tends to prevent foaming. In all 3 of these applications the $ClO_2$ releasing gel mixture would produce excellent disinfection, cleansing and deodorizing. The pH would be about 5 to 5.5 in these applications to more closely simulate the pH of the skin.

The present invention clearly represents an unexpected result in comparison to the teachings of the prior art. The closest prior art, the '514 patent, describes a chlorine dioxide containing composition comprising sodium chlorite and an "initiator" which promotes the release or formation of $ClO_2$. The composition described in the patent is a "thickened, one part, chlorine dioxide cleaner" (10–58). The viscosity of the described composition in about 1 week is between 100 and 300 cps (table I, IV, and VII), and is a slightly viscous, free flowing solution, rather than a gel. For use as initiators and thickeners the patent utilizes many common gelling agents, and perfumes, but as a $ClO_2$ initiator, it also mentions xanthan gum. The inventor never realized however, that xanthan gum when incorporating chlorite is the only gelling agent that is stable in both viscosity and pH, and releases no $ClO_2$ over time. The present discovery is particularly unexpected in light of the teachings of the '514 patent. It is noted here that the inventor of the '514 patent probably did not realize that xanthan gum alone among the number of "initiators" was not an initiator at all, but actually was stable to chlorite salt. It is believed that the inventor of the '514 subject matter could not easily have determined whether certain compounds are "initiators" or not, since at a pH below 10 (as in compositions described in his patent) chlorite would not be stable under normal conditions, alone or in combination with other chemicals. Even in deionized water, chlorite will degrade to chlorine dioxide, chloride or chlorate, depending upon the pH, and the temperature and amount of light. Furthermore, the release of $ClO_2$ is also catalyzed by the presence of sodium chloride and which is present in commercial sodium chlorite at a concentration of about 15%. This fact may also explain the untoward results posited by the '514 patent.

In clear contrast to the teachings of the art, the present invention uses xanthan successfully as the gelling and stabilizing agent for the synthesis of a viscous chlorite gel. This gel, moreover, may contain a much higher concentration of active ingredient, chlorite, than in the '514 patent. This is clearly an unexpected result.

In the present invention, the preferred viscosity of xanthan gum containing compositions ranges from about 20,000–25,000 cps rather than about 200 in '514. The gel of the present invention is not to be used alone as is the '514 composition, but instead is mixed with the acid Part B to release substantial quantities of $ClO_2$. The pH of our chlorite gel is at least about 11.0, preferably about 12.5, well above the 9.6 shown in '514. The concentration of $ClO_2$ in our activated gel is preferably at least about 5 ppm, more preferably at least about 100 ppm, even more preferably about 125 ppm or more, versus the 2 parts per million preferred in the '514 patent (7–9). Further, unlike the '514 patent, the viscosity of our xanthan gel has little bearing on the release of chlorine dioxide, such release (as shown in equation 1) depending heavily upon the initial pH of the mixed two part composition A+B.

The active chlorite ingredient according to '514 can control the release of chlorine dioxide (7–16). However, our xanthan chlorite gel remains stable, and both pH and viscosity do not appreciably change even with a chlorite active ingredient level of 2% or higher. Most importantly, no mention is made in the '514 patent of the effect of pH and the requirement of an acid pH to release chlorine dioxide, which is the most important indicator of $ClO_2$ release.

An exception to the statement that chlorite is unstable below 10.5 pH is a chlorite product available commercially known as "stabilized chlorine dioxide". It is a liquid chlorite complex with a pH of about 8, and the compound is in this case, stable. The chlorite molecule is complexed with sodium carbonate peroxide (U.S. Pat. No. 3,271,242), and then heavily buffered just above pH 8. There is no chlorine dioxide available in "stabilized chlorine dioxide" under normal use conditions. A strong acid at pH 1 or below is necessary to release chlorine dioxide from the buffered complex. This novel chlorite compound is mostly used as a mouthwash, and although the chlorite has oxidizing ability itself, there is no chlorine dioxide involved in the cleaning or deodorizing process.

Having generally described the invention, reference is now made to the following examples which are intended to illustrate preferred embodiments and comparisons. The included examples are not to be construed as limiting the scope of this invention as is more broadly set forth above and in the appended claims.

EXAMPLES

Example 1

Skin Protectant

| Component | Weight Percent |
|---|---|
| Part A | |
| Keltrol | 2% |
| Sodium Chlorite | 2% |
| Sodium Hydroxide | 0.36% |
| DI Water | Q.S. 100 |
| Part B | |
| Keltrol | 2% |
| Glycerin | 40% |
| Phosphoric Acid | 1.3% |
| Nacconol 90G | 0.2% |
| Glutaraldehyde | 0.03% |
| Fragrance | 0.02% |
| DI Water | Q.S. 100 |

Comments:
1. Components are added in the order listed and then mixed to homogeneity.
2. Glycerine is added as a skin protectant to the composition.
3. Nacconol is a preferred wetting agent.
4. Glutaraldehyde is added as a disproportionation agent to catalyze the release of $ClO_2$ so that the gel may be used immediately upon mixing parts A and B.

Example 2

Gel Wound Disinfectant

| Component | Weight Percent |
|---|---|
| Part A | |
| Keltrol | 2% |
| Sodium Chlorite | 2% |
| Sodium Hydroxide | 0.36% |
| DI Water | Q.S. 100 |
| Part B | |
| Keltrol | 2% |
| Glycerin | 10% |
| Phosphoric acid 85% | 1.3% |
| Nacconol 90G | 0.2% |
| Glutaraldehyde | 0.03% |
| DI Water | Q.S. 100 |

Comments: Same as for example 1, above.

Example 3

Ciderm Gel Soap

| Component | Weight Percent |
|---|---|
| Part A | |
| Keltrol | 1.25% |
| Sodium Chlorite | 2% |
| Sodium Hydroxide | 0.05% |
| DI Water | Q.S. 100 |
| Part B | |
| Keltrol | 1.25% |
| Glycerin | 16% |
| Phosphoric acid | 0.48% |
| Nacconol 90G | 4% |
| Fragrance | 0.12% |
| DI Water | Q.S. 100 |

Comments: Same as for example 1, above.

It is to be understood by those skilled in the art that the foregoing description and examples are illustrative of practicing the present invention, but are in no way limiting. Variations of the detail presented herein may be made without departing from the spirit and scope of the present invention as defined by the following claims.

I claim:

1. A storage stable chlorine dioxide generating composition in two parts to be mixed together to generate chlorine dioxide comprising a chlorite-containing part (A) and an acid-containing part (B), said chlorite-containing part (A) consisting essentially of an aqueous solution of about 0.1% to about 5% by weight of a water-soluble chlorite salt and an amount of xanthan gum as a gelling agent effective to gel said solution, said solution having a pH ranging from about 11.0 to about 13.0. said acid-containing part (B) comprising an amount of a protic acid in solution effective to produce an initial pH upon combining and mixing said parts A and B of less than about 5.5 and an amount of an acid stable gelling agent effective to gel said part B, said parts A and B being storage stable for a period of at least about 6 months.

2. The composition according to claim 1 wherein said acid stable gelling agent is selected from the group consisting of galactomannan, guar gum and locust bean (carob) gum, polyoxyalkylene crosslinked acrylic polymers, hydroxymethyl cellulose, hydroxypropyl cellulose, hydroxyethyl cellulose, methyl cellulose, methylpropyl cellulose, high molecular weight polyethylene glycols, polyacrylamide gels, crosslinked polyvinylpyrrolidones, and mixtures, thereof.

3. The composition according to claim 1 wherein said chlorite salt is sodium chlorite or potassium chlorite.

4. The composition according to claim 1 wherein said acid is selected from the group consisting of hydrochloric acid, sulfuric acid, nitric acid, benzenesulfonic acid, citric acid, fumaric acid, glycolic acid, lactic acid, malic acid, maleic acid, tartaric acid, citric acid, propionic acid, acetic acid, mandelic acid, sodium bisulfate, potassium bisulfate, phosphoric acid, and mixtures thereof.

5. The composition according to claim 1 wherein said gelling agent in said acid-containing part B is xanthan gum.

6. The composition according to claim 1 wherein said acid is phosphoric acid and said initial pH ranges from about 2.0 to about 4.5.

7. The composition according to claim 1 wherein said initial pH ranges from about 3.0 to about 4.5.

8. The composition according to claim 1 wherein said chlorite-containing part A comprises about 0.5% to about 3.0% by weight of sodium chlorite or potassium chlorite.

9. The composition according to claim 1 further comprising at least one additional component selected from the group consisting of disproportionation agents, surfactants, emollients, wound healing agents, lubricants, film-formers, diluents, fillers, humectants, fragrances, flavorings and skin penetrants.

10. The composition according to claim 8 wherein said initial pH ranges from about 2.8 to about 4.5, said acid is phosphoric acid, said gelling agent in said parts A and B is xanthan gum and said composition is storage stable for a period of at least about one year at room temperature.

11. A composition according to claim 1 wherein said chlorite containing part A and said acid containing part B are mixed.

12. A method of increasing the storage stability of a two part chlorine dioxide generating composition to be mixed together to generate chlorine dioxide in a mixed composition having a viscosity of at least about 100 cps, said two part storage stable chlorine dioxide generating composition comprising a chlorite-containing part (A) and an acid-containing part (B), said chlorite-containing part (A) consisting essentially of an aqueous solution of about 0.1% to about 5% by weight of a water-soluble chlorite salt at a pH ranging from about 11.0 to about 13.0 and said acid-containing part (B) comprising an amount of a protic acid in solution effective to produce an initial pH upon combining and mixing said parts A and B of less than about 5.5, said method comprising including in said chlorite-containing part A an amount of xanthan gum as a agelling agent effective to gel said chlorite containing part A and an amount of an acid stable gelling agent effective to gel said acid-containing part B, said composition being storage stable for a period of at least about 6 months.

13. The method according to claim 12 wherein said acid stable gelling agent is selected from the group consisting of galactomannan, guar gum and locust bean (carob) gum, polyoxyalkylene crosslinked acrylic polymers, hydroxymethyl cellulose, hydroxypropyl cellulose, hydroxyethyl cellulose, methyl cellulose, methylpropyl cellulose, high molcuelar weight polyethylene glycols, polyacrylamide gels, crosslinked polyvinylpyrrolidones, and mixtures, thereof.

14. The method according to claim 12 wherein said chlorite salt is sodium chlorite or potassium chlorite.

15. The method according to claim 12 wherein said acid is selected from the group consisting of hydrochloric acid, sulfuric acid, nitric acid, benzenesulfonic acid, citric acid, fumaric acid, glycolic acid, lactic acid, malic acid, maleic acid, tartaric acid, citric acid, propionic acid, acetic acid, mandelic acid, sodium bisulfate, potassium bisulfate, phosphoric acid, and mixtures thereof.

16. The method according to claim 12 wherein said acid is phosphoric acid and said initial pH ranges from about 2.0 to about 4.5.

17. The method according to claim 12 wherein said initial pH ranges from about 3.0 to about 4.5.

18. The method according to claim 12 wherein said chlorite-containing part A comprises about 0.5% to about 3.0% by weight of sodium chlorite or potassium chlorite.

19. The method according to claim 12 further comprising at least one additional component selected from the group consisting of disproportionation agents, surfactants, emollients, wound healing agents, lubricants, film-formers, diluents, fillers, humectants, fragrances, flavorings and skin penetrants.

20. The method according to claim 12 wherein said initial pH ranges from about 2.8 to about 4.5, said acid is phosphoric acid and said gelling agent is xanthan gum.

* * * * *